United States Patent [19]

Cherubim et al.

[11] 3,944,559

[45] Mar. 16, 1976

[54] PROCESS FOR THE PRODUCTION OF ALKYL-SUBSTITUTED UNSATURATED δ-LACTAMS

[75] Inventors: Martin Cherubim, Rheinkamp-Eick; Faisal Abodagga, Rheinkamp-Utfort, both of Germany

[73] Assignee: Deutsche Texaco Aktiengesellschaft, Hamburg, Germany

[22] Filed: Sept. 7, 1973

[21] Appl. No.: 395,307

[30] Foreign Application Priority Data
Sept. 14, 1972 Germany............................ 2245097

[52] U.S. Cl............................................. 260/297 Z
[51] Int. Cl.$^2$............... C07D 201/08; C07D 211/30
[58] Field of Search ................................. 260/297 Z

[56] References Cited
UNITED STATES PATENTS 3,267,111  8/1966  Vill................................. 260/297 Z
3,393,199  7/1968  Daum et al..................... 260/297 Z

OTHER PUBLICATIONS

Klingsberg, Pyridine and Derivatives, Part III, pp. 519–520, Interscience Publishers Inc., (1962).

*Primary Examiner*—John D. Randolph
*Attorney, Agent, or Firm*—T. H. Whaley; C. G. Ries; Kenneth R. Priem

[57] ABSTRACT

Alkyl-substituted unsaturated δ-lactams are obtained by contacting monocyanoethylated ketones with an aqueous acid solution and permitting them to react. Alkyl-substituted unsaturated δ-lactams of this invention are valuable intermediate products useful for organic synthesis in the production of pharmaceuticals and plastics.

5 Claims, No Drawings

PROCESS FOR THE PRODUCTION OF ALKYL-SUBSTITUTED UNSATURATED δ-LACTAMS

This application is related to our copending application Ser. No. 447,710, filed Mar. 4, 1974.

BACKGROUND OF THE INVENTION

1. Field of the Invention

The invention relates to a process for producing alkyl-substituted unsaturated lactams.

2. Discussion of the Prior Art

It is known to produce lactams from amino acids by splitting off water. However, the amino acids that are suitable for this process quite often are not readily available. One prior art process comprises hydrogenating alkyl-substituted phenols to alkyl-substituted cyclohexanols, dehydrogenating the cyclohexanols to the corresponding ketones, forming oximes and subjecting them to the Beckmann rearrangement, to obtain alkyl-substituted lactams. This procedure is troublesome and uneconomical.

Surprisingly, it was found that alkyl-substituted unsaturated δ-lactams are obtained by contacting the suitable monocyanoethylated ketones with an aqueous acid solution and permitting them to react.

SUMMARY OF THE INVENTION

The invention is a process for the production of alkyl-substituted unsaturated δ-lactams represented by the general formula:

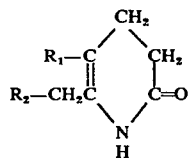

in which $R_1$ may be hydrogen or alkyl and $R_2$ may be hydrogen or alkyl. The process comprises admixing one mole of a monocyanoethylated ketone of the general formula

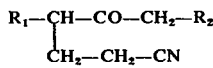

in which $R_1$ may be hydrogen or alkyl and $R_2$ may be hydrogen or alkyl, with concentrated mineral acid in an aqueous or aqueous-alcoholic solution and permitting the mixture to react. The invention is also the product of the reaction.

DESCRIPTION OF THE PREFERRED EMBODIMENTS

The reaction preferably takes place at a temperature of from about 40°C. to reflux temperature. After cooling the reacted mixture, the lactam may be recovered by extracting it from the reaction mixture. Examples of the mineral acid to be used are concentrated sulfuric acid and concentrated phosphoric acid. A monocyanoethylated ketone of the above-mentioned formula, in which $R_1$ and $R_2$ represent hydrogen or alkyl having from 1 to 5 carbon atoms, especially from 1 to 3 carbon atoms, is preferred.

A particular embodiment of the invention comprises diluting one mole of a ketone of the above-mentioned formula with from 30 to 500 ml of water or a water-alcohol mixture containing up to 90 parts of alcohol, preferably an aliphatic alcohol having from 1 to 4 carbon atoms, adding from 1 to 150 ml of concentrated sulfuric acid dropwise within a period of time of from 3 to 60 minutes, and subsequently permitting the mixture to react from 1 to 60 minutes at reflux temperature. Thereafter, the reaction mixture is cooled down quickly and worked up to recover the lactam.

It is known that if dicyanoethylated ketones are admixed with alkaline solutions bicyclical lactams are obtained. Properly considered, one could have expected to obtain, under the same or similar conditions, monocyclical lactams from monocyanoethylated ketones. But all attempts made to that effect failed. Consequently, it was most surprising to see such a cyclization take place under the indicated conditions. The structure of the compounds obtained according to this invention was ascertained by carbon, hydrogen, nitrogen analysis (CHN), nuclear magnetic resonance (NMR) and infared (IF) spectrographic analysis.

The process of this invention is suited to produce the alkyl-substituted unsaturated δ-lactams of the general formula indicated above in pure form and good yields and in a rapid manner. These compounds are valuable and interesting intermediate products useful for organic syntheses, for the production of pharmaceuticals and plastics.

The invention is further illustrated by the following example.

EXAMPLE

One mole (125 g) of monocyanoethylated methyl ethyl ketone (3-mono-(β-cyanoethyl)-butanone-2Thereafter, is diluted with 70 ml of water. Thereafer, 140 ml of concentrated sulfuric acid are added dropwise to the mixture with stirring over a period of 5 minutes, whereby the mixture is heated to reflux temperature. The reaction is continued for an additional 8 minutes at the indicated temperature. Subsequently, the reaction mixture is poured into ice water and extracted five times with 250 ml of diethyl ether. The extracts are combined, washed with water and dried with $CaCl_2$. This is followed by evaporating the ether and subjecting the remaining residue to fractionation at 0.008 inches of mercury. At a temperature between 100° and 110°C. a uniform, water-white liquid is obtained, which crystallizes immediately upon cooling. The mass of crystals is recrystallized from ethyl acetate. Colorless crystals are obtained having a melting point in the range of from 128° to 130°C. The yield is 83.8 percent of the theoretical value.

By CHN, NMR and IR analyses the obtained compound was established to be 3,4-dimethyl-2-azacyclohexene(3)-one of the formula:

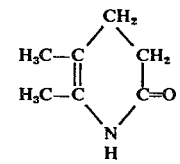

We claim:

1. A process for preparing 3,4 dimethyl-2-aza-cyclohexene (3)-one of the formula:

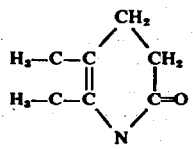

comprising reacting 3-mono-β—cyanoethyl-butanone-2 with a mixture consisting of a strong mineral acid in an aqueous or aqueous-alcoholic solution.

2. A process as in claim 1 wherein the temperature of the reaction mixture is from about 40°C to reflux temperature.

3. A process as in claim 1 wherein the mineral acid is concentrated sulfuric acid.

4. A process as in claim 1 wherein the mineral acid is concentrated phosphoric acid.

5. A process for preparing 3,4-dimethyl-2-aza-cyclohexene (3)-one of the formula

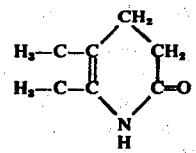

comprising reacting 3-mono-β-cyanoethyl-butanone-2 with a mixture consisting of concentrated sulfuric acid in an aqueous solution.

* * * * *